(12) United States Patent
Reinhard et al.

(10) Patent No.: US 7,511,036 B2
(45) Date of Patent: Mar. 31, 2009

(54) DIHYDROTHIAZINE PRODRUGS OF THIAZOLIUM AGENTS

(75) Inventors: Emily Reinhard, Ridgewood, NJ (US); Elliot Katten, Flushing, NY (US)

(73) Assignee: Synvista Therapeutics, Inc., Montvale, NJ (US)

( * ) Notice: Subject to any disclaimer, the term of this patent is extended or adjusted under 35 U.S.C. 154(b) by 0 days.

(21) Appl. No.: 11/390,946

(22) Filed: Mar. 27, 2006

(65) Prior Publication Data

US 2007/0054901 A1    Mar. 8, 2007

Related U.S. Application Data

(63) Continuation of application No. 10/824,848, filed on Apr. 15, 2004, now abandoned.

(60) Provisional application No. 60/463,807, filed on Apr. 18, 2003.

(51) Int. Cl.
| | |
|---|---|
| C07D 279/12 | (2006.01) |
| A61K 31/54 | (2006.01) |
| A61K 31/541 | (2006.01) |
| A61K 31/426 | (2006.01) |

(52) U.S. Cl. ............... 514/227.5; 544/56; 544/58.5; 544/58.6; 544/58.7; 514/227.8

(58) Field of Classification Search .......... 544/56, 544/58.5, 58.6, 58.7; 514/227.5, 227.8
See application file for complete search history.

(56) References Cited

U.S. PATENT DOCUMENTS

| 4,609,970 | A | * | 9/1986 | Hilpert ............... 361/757 |
| 4,683,312 | A | | 7/1987 | Dominianni et al. ...... 548/341 |
| 4,758,583 | A | | 7/1988 | Cerami et al. .......... 514/399 |
| 5,108,930 | A | | 4/1992 | Ulrich et al. ........... 436/111 |
| 5,230,998 | A | | 7/1993 | Neurath et al. .......... 435/7.1 |
| 5,262,152 | A | | 11/1993 | Ulrich et al. .............. 424/54 |
| 5,366,885 | A | | 11/1994 | Barranco, III et al. ........ 435/6 |
| 5,656,261 | A | | 8/1997 | Cerami et al. ............ 424/53 |
| 5,850,840 | A | | 12/1998 | Cerami et al. ............ 131/330 |
| 5,853,703 | A | | 12/1998 | Cerami et al. | |
| 5,854,000 | A | | 12/1998 | Bucala et al. ............. 435/7.1 |
| 6,007,865 | A | | 12/1999 | Cerami et al. ............ 426/656 |
| 6,121,300 | A | | 9/2000 | Wagle et al. ............ 514/365 |
| 6,440,749 | B1 | | 8/2002 | Cerami et al. | |
| 2002/0068729 | A1 | | 6/2002 | Egan et al. | |
| 2002/0160993 | A1 | | 10/2002 | Egan et al. | |
| 2004/0034074 | A1 | | 2/2004 | Cerami et al. | |

FOREIGN PATENT DOCUMENTS

| DE | 2 323 465 | 11/1973 |
| EP | 0 167 139 A1 | 1/1986 |
| EP | 0 170 037 A2 | 2/1986 |
| EP | 0 364 344 A2 | 4/1990 |
| EP | 0 586 806 A1 | 3/1994 |
| EP | 0 614 886 A1 | 9/1994 |
| JP | 60-184038 | 9/1985 |
| JP | 1-143855 | 6/1989 |
| WO | 94/11490 | 5/1994 |

OTHER PUBLICATIONS

Adam, et al., *Tetrahedron Lett.*, 36:3063-3066 (1969).
Archer, et al., *J. Med Chem.*, 22(3):306-309 (1979).
Asif, et al., *Proc. Natl. Acad. Sci. USA*, 97(6):2809-2813 (2000).
Brown, R.D., *J. Theor. Biol.*, 143:565-573 (1990).
Brownlee, et al., *Diabetes*, (Suppl 1) 42A, Abstract 166 (1986).
Brownlee, et al., *Science*, 232:1629-1632 (1986).
Bucala, et al., *Advances in Pharmacol.*, Academic Press, 23:1-34 (1992).
Chang et al., *J. Biol Chem.*, 260(13):7970-7974 (1985).
Crosby, et al., *J. Am. Chem. Soc.*, 92(9):2891-2900 (1970).
Dominianni, et al., *J. Med. Chem.*, 32:2301-2306 (1989).
Eble, et al., *J. Biol. Chem.*, 258(15):9406-9412 (1983).
Galera, et al., *J. Heterocyclic Chem.*, 23:1889-1892 (1986).
Gandasegui, et al., *Heterocycles*, 31:1801-1809 (1990).

(Continued)

*Primary Examiner*—Kahsay T Habte
(74) *Attorney, Agent, or Firm*—Ivor R. Elrifi; Matthew Pavao; Mintz, Levin, Cohn, Ferris, Glovsky and Popeo, P.C.

(57) ABSTRACT

Provided are compounds of the formula (and pharmaceutically acceptable salts thereof):

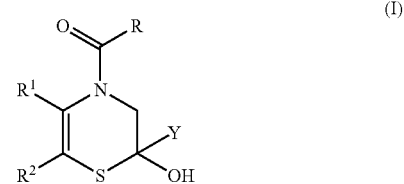

(I)

wherein:
R is hydrogen, methyl, hydroxymethyl or α-hydroxyethyl;
$R^1$ and $R^2$ are independently selected from hydrogen, $C_1$-$C_6$ alkyl, $C_1$-$C_6$ hydroxyalkyl, $C_3$-$C_8$ cycloalkyl, $C_1$-$C_6$ alkenyl, $C_1$-$C_6$ alkynyl, amino, monoalkylamino, dialkylaminoalkyl, and pyrrolidin-1-ylalkyl; and Y is selected from the group consisting of $C_1$-$C_6$ alkyl, substituted and unsubstituted aryl; with the provisos that: (a) if Y is aryl, then at least one of $R^1$ and $R^2$ is other than hydrogen, and (b) if $R^2$ is hydrogen $R^1$ is other than methyl.

Also provided are pharmaceutical compositions containing the compounds, and methods for the preparation of the compounds. The compounds are useful, among other things, as prodrugs which can be converted under acidic conditions to thiazolium agents. The compounds can be administered to mammals, including humans, for treatment of various indications.

28 Claims, No Drawings

OTHER PUBLICATIONS

Hayase, et al., *J. Biol. Chem.*, 263(7):3758-3764 (1989).
Hopmann, R.F.W., *Ann. N.Y. Acad. Sci., Alkali-Induced Transformations*, pp. 32-50 (1982).
Inoge, et al., *J.C.S. Chem. Comm.*, 12:549-550 (1980).
Kass, et al., *Circulation*, 104:r8-r14 (2001).
Kawakishi et al., *Maillard Reactions Chem. Food Health.*, 151:2881-285 (1994).
Kibirev, et al., *Ukranian Journal of Chemistry*, 30(5):488-495 (1964) (English Translation provided).
Kluger, et al., *J. Am. Chem. Soc.*, 103(4):884-888 (1981).
Makita, et al., *J. Biol. Chem.*, 267(8):5133-5138 (1992).
Marcaccini, et al., *Tetrahedron Lett.*, 43:8591-8593 (2002).
Mizuhara, et al., *J. Am. Chem. Soc.*, 76:571-573 (1954).
Monn, et al., *J. Org. Chem.*, 59:2773-2778 (1994).
Nicholls, et al., *Lab. Invest.*, 60(4):486-491 (1989).
Nordbo, H., *J. Dent. Des.*, 58(4):1429 (1979).
Oimomi, et al., *Agric. Biol Chem.*, 53(6):1727-1728 (1989).
Oimomi, et al., *Diabetes Res. Clin. Pract.*, 6(4):311-313 (1989).
Pongor, et al., *Proc. Natl Acad. Sci. USA*, 81:2684-2688 (1984).
Potts, et al., *J. Org. Chem.*, 41(2):187-191 (1976).
Potts, et al., *J. Org. Chem.*, 42(9):1648-1649 (1977).
Schoenafinger, et al., *Chem. Abstracts*, Abstract No. 173495q, 120:682 (1994).
Sell, et al., *J. Biol. Chem.*, 264(36):21597-21602 (1989).
Sheehan, et al., *J. Org. Chem.*, 39(9):1196-1199 (1974).
Singh, et al., *Tetrahedron*, 48(22):4545-4550 (1992).
Sohda, et al., *Chem. Abstracts*, Abstract No. 132169y, 113:652 (1990).
Sohda, et al., *Chem. Abstracts*, Abstract No. 191334w, 113:723 (1990).
Tagaki, et al., *Bull. Chem. Soc. Jpn.*, 53(2):478-480 (1980).
Takamizawa, et al., *J. Org. Chem.*, 33(11):4038-4045 (1968).
Takamizawa, et al., *Tetrahedron Lett.*, 37:4027-4030 (1968).
Tamura, et al., *Synthesis*, 1:1-17 (1977).
Thornalley, et al., *Biochem. Pharmacol*, 57:303-307 (1999).
Tsuge, et al., *Chem. Lett.*, 5:711-714 (1982).
Ulrich, et al., *Modern Aging Res.*, 7:83-92 (1985).
Voller, et al., *Alternative Immunoassays*, Chapter 6, pp. 77-86 (1985).
Vovk, et al., *Ukranian Journal of Chemistry*, 51:521-525 (1985).
Washabaugh, et al., *Bioorganic Chem.*, 20:296-312 (1992).
Wolffenbuttel, et al., *Proc. Natl. Acad. Sci. USA*, 95:4630-4634 (1998).
Yamazaki, et al., *Chem. Pharm. Bull.*, 40(4):1025-1028 (1992).
Yang, et al., *Arch. Biochem. Biophys.*, 412:42-46 (2003).
Yoshimura, et al., *Chem. Abstracts*, Abstract No. 15815y, 119:12 (1993).

* cited by examiner

DIHYDROTHIAZINE PRODRUGS OF THIAZOLIUM AGENTS

RELATED APPLICATIONS

This patent application is a Continuation of U.S. Patent Application No. 10/824,848, filed Apr. 15, 2004 (now abandoned), which claims priority to U.S. Provisional Application Ser. No. 60/463,807, filed Apr. 18, 2003. The contents of these applications are each incorporated by reference in their entirety.

FIELD OF THE INVENTION

The present invention relates to certain N-formyl and N-acyl dihydrothiazine compounds that are useful, among other things, as prodrugs which can be converted under acidic conditions to thiazolium agents. The N-formyl and N-acyl dihydrothiazines can be administered to mammals, including humans for the treatment of a number of indications including hypertension, reduced vascular compliance, diastolic dysfunction and heart failure.

BACKGROUND OF THE INVENTION

Glucose and other sugars react with proteins by a non-enzymatic, post-translational modification process called non-enzymatic glycation. At least a portion of the resulting sugar-derived adducts, called Amadori products, mature to a molecular species that is very reactive, and can readily bind to amino groups on adjacent proteins, resulting in the formation of cross-links between proteins. These sugar derived cross-links can undergo further reaction which lead to the formation of advanced glycated end products (AGEs) some of which may be difficult to break either chemically or enzymatically. Recently a number of classes of compounds have been identified whose members inhibit the formation of the cross-links, or in some cases break the cross-links. These compounds include, for example, the thiazolium compounds described in U.S. Pat. No. 5,853,703. If allowed to accumulate, AGEs, and particularly the resulting cross-links, can lead to several degradations in body function linked with diabetes or age. The above mentioned thiazolium compounds have been used, with success, in animal models for such indications. These indications include loss of elasticity in blood vasculature, loss of kidney function and the appearance of retinopathy.

In addition, as part of studies on these compounds, it has been identified that these thiazolium compounds inhibit the formation of bioactive agents, such as growth factors and inflammatory mediators, that are associated with a number of indications. These agents include vascular endothelial growth factor (VEGF) and TGF[beta]. As a result, a number of new indications have been identified for treatment with agents that inhibit the formation of, or more preferably break cross-links associated with the AGE process. It is not unreasonable to infer that the effects seen are due to the removal of AGE-related molecules that provide a stimulus for the production or release of these growth factors. Removal of such molecules is believed to proceed in part due to the elimination of cross-links that lock the AGE-modified proteins in place. Moreover, such thiazolium compounds also reduce the expression of collagen in conditions associated with excess collagen production.

New methods for administering certain of the above-described thiazolium agents offer researchers additional tools to address pharmacokinetic issues. In addition to having a number of formulations of the thiazolium agents themselves available, it would also be desirable to have prodrugs that are readily converted under physiological conditions to thiazolium agents that can prevent the formation of, and break AGE-crosslinks. Among other things, prodrugs offer the potential for altering certain properties of the agents so that they are more suitable to the conditions in a particular body tissue, cavity or fluid than the drug itself. For example, the prodrug can possess a more advantageous solubility and ionizability profile for a particular body fluid or route of administration than the drug itself. In addition absorption across certain tissues, e.g., skin, mucous membranes can be improved. Such improvements in the physical properties of the agent can contribute to improved delivery of the agent to the site of action, resulting in lower doses of the administered agent. Moreover, having available prodrugs with different physical and chemical properties than the drug itself offers additional chemical entities for preparing pharmaceutical formulations.

SUMMARY OF THE INVENTION

In one aspect, the invention relates to a compound of the formula:

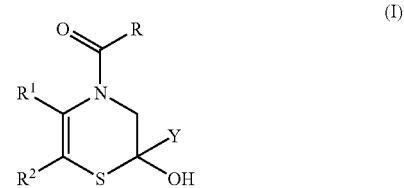

(I)

wherein:

R is hydrogen, methyl, hydroxymethyl or α-hydroxyethyl;

$R^1$ and $R^2$ are independently selected from hydrogen, $C_1$-$C_6$ alkyl, $C_1$-$C_6$ hydroxyalkyl, $C_3$-$C_8$ cycloalkyl, $C_1$-$C_6$ alkenyl, $C_1$-$C_6$ alkynyl, amino, monoalkylamino, dialkylaminoalkyl, and pyrrolidin-1-ylalkyl; and Y is selected from the group consisting of $C_1$-$C_6$ alkyl, substituted and unsubstituted aryl;

with the provisos that:

(a) if Y is aryl, then at least one of $R^1$ and $R^2$ is other than hydrogen, and (b) if $R^2$ is hydrogen $R^1$ is other than methyl; or a pharmaceutically acceptable salt thereof.

In one preferred embodiment, $R^1$ and $R^2$ are independently selected from $C_1$-$C_6$ alkyl, $C_1$-$C_6$ hydroxyalkyl, $C_3$-$C_8$ cycloalkyl, $C_1$-$C_6$ alkenyl, $C_1$-$C_6$ alkynyl, amino, monoalkylamino, dialkylaminoalkyl, and pyrrolidin-1-ylalkyl. Preferably, R is selected from hydrogen, hydroxymethyl or α-hydroxyethyl. Preferably, at least one of $R^1$ and $R^2$ is $C_1$-$C_6$ alkyl, preferably methyl.

In one preferred embodiment, Y is selected from the group consisting of substituted phenyl and, in particular, unsubstituted phenyl. For example, preferred compounds include compounds wherein Y is unsubstituted phenyl; R is hydrogen; and $R^1$ and $R^2$ are both methyl. In other exemplary preferred compounds, Y is unsubstituted phenyl; R is α-hydroxyethyl; and $R^1$ and $R^2$ are both methyl. X is preferably chloride or bromide in these preferred compounds.

Other preferred compounds of the invention are those where at least one of $R^1$ and $R^2$ is $C_1$-$C_6$ hydroxyalkyl, more preferably 2-hydroxyalkyl.

In another preferred embodiment, Y is selected from the group consisting of substituted and unsubstituted heteroaryl. Preferred heteroaryl groups include substituted and unsubstituted pyrrolyl, furyl, thienyl, 1-methylimidazoly-2-yl and 4,6-(bis-pyrrolidin-1-yl)-pyrimidin-2-yl.

Where Y is substituted aryl, the substitutions of aryl are preferably one to three substituents selected from amino; $C_1$-$C_6$ alkylamino; $C_1$-$C_6$ dialkylamino; $C_1$-$C_6$ alkoxy, $C_1$-$C_6$ alkyl; cyano; nitro; $C_1$-$C_6$ mono-, di- or trifluoroalkyl (particularly $C_1$-$C_6$ trifluoroalkyl); nitro; fluoro; chloro and bromo.

Another aspect of the invention relates to a pharmaceutical composition comprising a pharmaceutically effective amount of a compound of the formula:

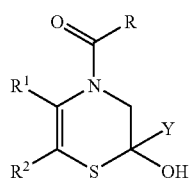

(I)

wherein:

R is hydrogen, methyl, hydroxymethyl or α-hydroxyethyl;

$R^1$ and $R^2$ are independently selected from hydrogen, $C_1$-$C_6$ alkyl, $C_1$-$C_6$ hydroxyalkyl, $C_3$-$C_8$ cycloalkyl, $C_1$-$C_6$ alkenyl, $C_1$-$C_6$ alkynyl, amino, monoalkylamino, dialkylaminoalkyl, and pyrrolidin-1-ylalkyl; and Y is selected from the group consisting of $C_1$-$C_6$ alkyl, substituted and unsubstituted aryl;

or a pharmaceutically acceptable salt thereof; and a pharmaceutically acceptable carrier.

In some preferred pharmaceutical compositions, at least one of $R^1$ and $R^2$ is other than hydrogen, and if $R^2$ is hydrogen $R^1$ is other than methyl in the compound of the formula I. For example, in one preferred pharmaceutical composition, R is hydrogen, $R^1$ and $R^2$ are both methyl and Y is unsubstituted phenyl in the compound of formula I. In another preferred embodiment, the composition contains a compound of the formula I wherein R is α-hydroxyethyl, $R^1$ and $R^2$ are both methyl, and Y is unsubstituted phenyl.

Another aspect of the invention relates to a method for preparing a compound of the formula:

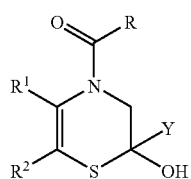

(I)

that includes treating a thiazolium compound of the formula:

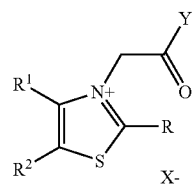

(II)

wherein:

R is hydrogen, methyl, hydroxymethyl or α-hydroxyethyl;

$R^1$ and $R^2$ are independently selected from hydrogen, $C_1$-$C_6$ alkyl, $C_1$-$C_6$ hydroxyalkyl, $C_3$-$C_8$ cycloalkyl, $C_1$-$C_6$ alkenyl, $C_1$-$C_6$ alkynyl, amino, monoalkylamino, dialkylaminoalkyl, and pyrrolidin-1-ylalkyl; and Y is selected from the group consisting of a substituted and unsubstituted aryl; and X— is an anion;

with the provisos that:

(a) if Y is aryl, then at least one of $R^1$ and $R^2$ is other than hydrogen, and (b) if $R^2$ is hydrogen $R^1$ is other than methyl;

with an aqueous alkaline solution to afford the compound of the formula I.

The method is preferably conducted using an aqueous alkaline solution having a pH of at least 8. For instance, the pH of the aqueous alkaline solution can be between 9 and 11.

In preferred embodiments of the method, R is hydrogen, $R^1$ and $R^2$ are both methyl and Y is unsubstituted phenyl in the compound of formula II.

In another aspect, the invention relates to a method for preparing a thiazolium compound of the formula:

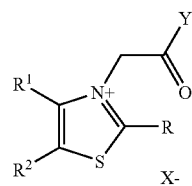

(II)

wherein

R is hydrogen, methyl, hydroxymethyl or α-hydroxyethyl;

$R^1$ and $R^2$ are independently selected from hydrogen, $C_1$-$C_6$ alkyl, $C_1$-$C_6$ hydroxyalkyl, $C_3$-$C_8$ cycloalkyl, $C_1$-$C_6$ alkenyl, $C_1$-$C_6$ alkynyl, amino, monoalkylamino, dialkylaminoalkyl, and pyrrolidin-1-ylalkyl;

Y is selected from the group consisting of $C_1$-$C_6$ alkyl, substituted and unsubstituted aryl; and X— is an anion;

with the provisos that:

(a) if Y is aryl, then at least one of $R^1$ and $R^2$ is other than hydrogen, and (b) if $R^2$ is hydrogen $R^1$ is other than methyl.

The method is conducted by treating a compound of the formula:

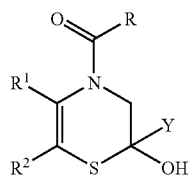
(I)

with an acidic solution to afford the thiazolium compound of the formula II.

In this method for forming the compound of the formula II, the acidic solution can be an aqueous 0.1 N to 10 N HCl solution. For example, the method can be conducted in the stomach, where the acidic solution is gastric juice.

As will be apparent to those of skill in the art, such acidic solutions can optionally contain some proportion of organic solvent to aid in the dissolution of the compound of formula I, in addition to an aqueous component.

In preferred embodiments of the method, $R^1$ and $R^2$ are both methyl in the compound of formula I. For example, in one particularly preferred embodiment of the method, R is hydrogen, $R^1$ and $R^2$ are methyl, and Y is unsubstituted phenyl. In another particularly preferred method, R is α-hydroxyethyl, $R^1$ and $R^2$ are methyl, and Y is unsubstituted phenyl. These methods are preferably conducted using an acidic solution of 1 N to 5 N hydrochloric acid.

In another preferred method for forming the compound of formula II, R is —CH(OH)CH$_3$, $R^1$ and $R^2$ are methyl and Y is unsubstituted phenyl in the compound of formula I.

Another aspect of the invention relates to a method of treating a mammal having an indication of the invention by administering an effective amount of the compound of the formula:

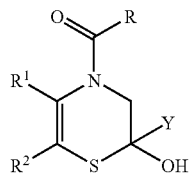
(I)

wherein:
R is hydrogen, methyl, hydroxymethyl or α-hydroxyethyl;
$R^1$ and $R^2$ are independently selected from hydrogen, $C_1$-$C_6$ alkyl, $C_1$-$C_6$ hydroxyalkyl, $C_3$-$C_8$ cycloalkyl, $C_1$-$C_6$ alkenyl, $C_1$-$C_6$ alkynyl, amino, monoalkylamino, dialkylaminoalkyl, and pyrrolidin-1-ylalkyl, and
Y is selected from the group consisting of $C_1$-$C_6$ alkyl, substituted and unsubstituted aryl;
with the provisos that:
(a) if Y is aryl, then at least one of $R^1$ and $R^2$ is other than hydrogen, and
(b) if $R^2$ is hydrogen $R^1$ is other than methyl;
or a pharmaceutically acceptable salt thereof to the mammal.

The indications of the invention that can be treated using the method described above include hypertension (e.g., isolated systolic hypertension and systolic hypertension), reduced vascular compliance, diastolic dysfunction and heart failure (including diastolic heart failure).

Another aspect of the invention relates to a method of treating a mammal having an indication of the invention, by administering an amount of the compound of the formula:

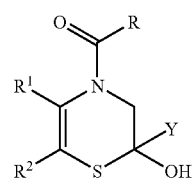
(I)

wherein:
R is hydrogen, methyl, hydroxymethyl or α-hydroxyethyl;
$R^1$ and $R^2$ are independently selected from hydrogen, $C_1$-$C_6$ alkyl, $C_1$-$C_6$ hydroxyalkyl, $C_3$-$C_8$ cycloalkyl, $C_1$-$C_6$ alkenyl, $C_1$-$C_6$ alkynyl, amino, monoalkylamino, dialkylaminoalkyl, and pyrrolidin-1-ylalkyl; and
Y is selected from the group consisting of $C_1$-$C_6$ alkyl, substituted and unsubstituted aryl;
or a pharmaceutically acceptable salt thereof;
that is effective to obtain a therapeutically effective amount of the compound of the formula:

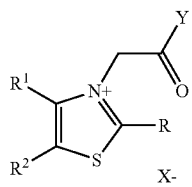
(II)

wherein:
R, $R^1$, $R^2$ and Y are as described above; and X— is an anion.

In some preferred embodiments of the method at least one of $R^1$ and $R^2$ is $C_1$-$C_6$ alkyl. For example, in some preferred embodiments of the method, Y is unsubstituted phenyl, R is hydrogen, and $R^1$ and $R^2$ are methyl in the administered compound.

In other preferred embodiments of the method, Y is unsubstituted phenyl. For instance, in some preferred embodiments of the method, Y is unsubstituted phenyl, R is α-hydroxyethyl, and $R^1$ and $R^2$ are methyl in the administered compound.

The indications of the invention that can be treated using the method described above include hypertension (e.g., isolated systolic hypertension and systolic hypertension), reduced vascular compliance, diastolic dysfunction and heart failure (including diastolic heart failure).

DEFINITIONS

"Alkyl" includes linear and branched alkyl groups, e.g., methyl, ethyl, t-butyl, and the like.

"Alkoxy" includes linear and branched alkoxy groups, e.g., methoxy, ethoxy, t-butyloxy, and the like.

"Alkenyl" includes linear and branched alkenyl groups.

"Aryl" alone or in combination, includes carbocyclic aromatic systems ($C_6$ or $C_{10}$) or a heterocyclic aromatic systems (also known as heteroaryl). The term "aryl" is thus deemed to include "heteroaryl". The systems may contain one, two or three rings wherein such ring may be attached together in a pendent manner or may be fused. Aryl can be unsubstituted or substituted as set forth above.

"Heteroaryl" refers to rings containing at least one and up to three atoms of N for the 6 membered heteroaryl ring. The 5 membered heteroaryl ring contains; (1) from one to three atoms of N, or (2) one atom of O or S and zero to two atoms of N. The heteroaryl is optionally substituted as set forth below. Nonlimiting examples of heteroaryl groups include: pyrrolyl, furanyl, thienyl, pyridyl, oxazolyl, pyrazolyl, pyrimidinyl, and pyridazinyl.

Aryl substitutions are one to three substituents selected from amino; $C_1$-$C_6$ alkylamino; $C_1$-$C_6$ dialkylamino; $C_1$-$C_6$ alkoxy; $C_1$-$C_6$ alkyl; cyano; nitro; $C_1$-$C_6$ mono-, di-, or trifluoroalkyl; nitro; fluoro; chloro and bromo.

DETAILED DESCRIPTION OF THE INVENTION

Provided are N-formyl or N-acyl dihydrothiazine compounds that are readily converted under acidic conditions to thiazolium agents that can prevent AGE crosslink formation, and can break existing crosslinks related to AGE formation. Such N-formyl and N-acyl dihydrothiazine compounds are simple to prepare.

N-formyl or N-acyl dihydrothiazine compounds of the formula I

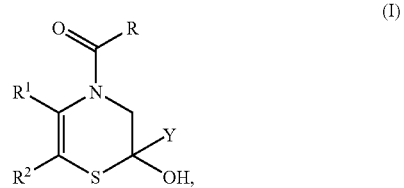

wherein R, $R^1$, $R^2$ and Y are as described above, readily convert to thiazolium agents under acidic conditions. Acidic conditions exist in certain body fluids such as gastric juice where the pH is approximately 2. Such conditions facilitate the conversion of the compounds of the formula I to thiazolium compounds.

An attractive feature of the N-formyl and N-acyl dihydrothiazine compounds of the formula I are that they are more lipophilic compounds than their isomeric thiazolium counterparts. The difference in the lipophilicity between these two classes of compounds may offer the clinician additional routes of administrations for delivering agents that prevent AGE crosslinks and break existing AGE crosslinks. For example, administration of more lipophilic agents can be preferable for certain delivering agents via transdermal, pulmonary and transmucosal formulations.

The N-formyl or N-acyl dihydrothiazine compounds are readily prepared by treatment of the desired thiazolium compound of the formula II

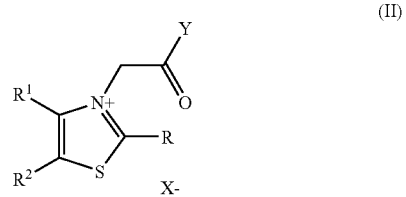

wherein R, $R^1$, $R^2$, and X are as described above, with a base effective to convert the thiazolium to an N-formyl or N-acyldihydrothiazine. Generally an aqueous alkaline solution (e.g., hydroxide solution, phosphate buffered alkaline solution) is used to effect the conversion. For example, treatment of 4,5-dimethyl-3-(2-oxo-2-phenylethyl)-thiazolium chloride with sodium hydroxide solution at room temperature provided 2-hydroxy-5,6-dimethyl-2-phenyl-2,3-dihydro-(1,4)thiazine-4-carbaldehyde.

Typically, such base mediated conversions are conducted in aqueous solutions. However, base alcoholic solutions can also be used. In several cases the product dihydrothiazine precipitates from the aqueous medium, and the product can be recovered by filtration. The recovered product can be further purified by, for example, recrystallization. Optionally, the product can be recovered by extraction with an immiscible organic solvent (which is stable to base) such as methylene or ethylene chloride or toluene.

Alternatively, the basic solution used in the conversion can contain some proportion of organic solvent to assist in the dissolution of the dihydrothiazine compounds. For example, such aqueous solutions can contain chloroform, methylene chloride or other halogenated solvents.

In an alternative preparation of the N-acyl or N-formyl dihydrothiazine compounds, the thiazine ring can be formed through condensation of acyclic precursors, such as thioglycine [$H_2N$—$CH_2C(O)SH$] and a ketone of the formula (III)

wherein LG is a leaving group (e.g., a halide such as chloro or bromo), and $R^1$ and $R^2$ are as described above, to provide a 1,4-thiazolin-2-one of the formula (IV)

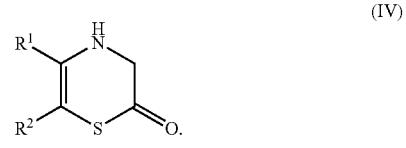

IV can then be treated with an acylating agent (e.g., acetic anhydride and the like) or a formylating agent (e.g., formyl acetic anhydride) to give a compound of the formula (V)

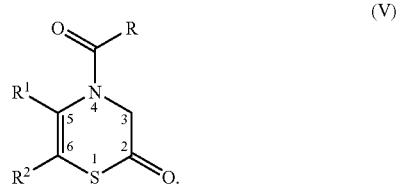

The Y group can be introduced at the 2 position of the ring by reaction of the thiolactone group of V with an appropriate organometallic agent such as an alkyl lithium cuprate reagent, aryl lithium cuprate reagent, alkyl Grignard reagent or aryl Grignard reagent to afford compounds of the formula I.

The compounds of the formula I contain a chiral carbon atom at position 2 of the dihydrothiazine nucleus. The present invention is meant to comprehend every stereoisomer of the compound of formula I including isolated optical isomers, and mixtures thereof (including pharmaceutically acceptable salts thereof). In addition, other chiral carbon atoms may also be present elsewhere in the compound so that diastereomers are formed. Here again, the invention is meant to comprehend every stereoisomer of such compounds.

Isolated optical isomers may be purified from racemic mixtures by well-known chiral separation techniques. According to one such method, a racemic mixture of a compound having the structure of formula I or chiral intermediate thereof, is separated into 99% wt. % pure optical isomers by HPLC using a suitable chiral column, such as a column containing a packing of chiral phase material bonded to silica gel.

The compounds of the formula I can be administered in the form of a pharmaceutical composition, in combination with a pharmaceutically acceptable carrier. The active ingredient in such formulations can comprise from 0.1 to 99.99 weight percent. By "pharmaceutically acceptable carrier" is meant any carrier, diluent or excipient which is compatible with the other ingredients of the formulation and is not deleterious to the recipient.

Provided is a method of treating or ameliorating an indication of the invention in an animal, preferably a mammal, more preferably a human, comprising administering an effective amount of a compound of the formula I or a pharmaceutically acceptable salt thereof.

Hypertension, Isolated Systolic Hypertension

Cardiovascular risk correlates more closely with the systolic and the pulse pressure than with the diastolic pressure. In diabetic patients, the cardiovascular risk profile of diabetic patients is strongly correlated to duration of diabetes, glycemic control and blood pressure. Structural matrix proteins contribute to the function of vessels and the heart, and changes in the physical behavior of cardiovascular walls are believed to be important determinants of circulatory function. In elderly individuals, the loss of compliance in the aorta leads to systolic hypertension and isolated systolic hypertension, which in turn expands the arterial wall and thereby diminishes the dynamic range of elasticity. In vivo studies in rodents, canines and in primates with an exemplary thiazolium compound, 3-[2-phenyl-2-oxoethyl]-4,5-dimethyl-thiazolium salt, indicate potential utility in substantially ameliorating vascular stiffening. For example, in a dog model for diabetes, lower end diastolic pressure and increased end diastolic volume, indicators of ventricular elasticity, returned to a value at about the mid-point between the disease impaired value and the value for control dogs. Treatment with 3-[2-phenyl-2-oxoethyl]-4,5-dimethyl-thiazolium salt lead to a reduction in the mass of collagen in cardiovascular tissues. In situ hybridization studies demonstrate that 3-[2-phenyl-2-oxoethyl]-4,5-dimethyl-thiazolium salt reduces the expression of both Type IV collagen and TGFbeta. In a phase IIa clinical trial, treatment with that 3-[2-phenyl-2-oxoethyl]-4, 5-dimethyl-thiazolium salt led to a reduction of left ventricular mass. These studies indicate that prodrugs of such thiazolium compounds should have a similar effect.

Compared with that of a non-diabetic, the diabetic artery is smaller as it is stiffer. As in systolic hypertension and isolated systolic hypertension in which vessels stiffen with age and lose the dynamic range of expansion under systole. The compounds of the invention are used to treat, prevent, reduce or ameliorate hypertension, including systolic hypertension, isolated systolic hypertension and diabetic hypertension. Moreover, the same benefit is anticipated for the more rare hypertensive disorder, pulmonary hypertension. Pulmonary hypertension is a rare blood vessel disorder of the lung in which the pressure in the pulmonary artery (the blood vessel that leads from the heart to the lungs) rises above normal levels and may become life threatening. The similarity in development of elevated blood pressure in the pulmonary bed with the increase in systemic blood pressure in diabetic hypertension and in isolated systolic hypertension suggests similar mechanisms are involved.

Pulse pressure is the difference between systolic and diastolic blood pressure. In a young human, systolic pressure is typically 120 mm Hg and diastolic pressure is 80 mm Hg, resulting in a pulse pressure of 40 mm Hg. With age, in many individuals pulse pressure increases, largely due to the increase in systolic pressure that results from stiff vessel disease. In individuals with pulse pressure greater than 60 mm Hg there is an increased risk of death from cardiovascular morbidities. In a Phase IIa trial, the compound, 3-[2-phenyl-2-oxoethyl]-4,5-dimethyl-thiazolium salt, reduced pulse pressure in elderly patients with pulse pressures greater than 60 mm Hg in a statistically significant manner. This decrease in pulse pressure was believed to be due primarily to the effect of the agent on lowering the systolic blood pressure.

The compounds of the invention are used to treat, prevent, reduce or ameliorate reduced vascular compliance, elevated pulse pressure, and hypertension. Moreover, the compounds are used to reduce pulse pressure, increase vascular compliance, or decrease the risk of death.

Increased blood pressure can lead to the development of hypertensive encephalopathy. Compounds of the invention are used to treat, prevent, reduce or ameliorate hypertensive encephalopathy.

Heart Failure

Congestive Heart Failure (CHF) is a clinical syndrome that entails cardiac disease of the ventricle. Diastolic dysfunction is a subset of heart failure in which the left ventricle stiffens with age. The stiffening of the left ventricle that occurs in CHF and in diastolic dysfunction is believed to result from increased crosslinking of collagen fibers with age and/or fibrosis and related hypertrophy. The compounds of the invention are used to treat, prevent, reduce or ameliorate heart failure and diastolic heart failure.

Arteriosclerosis, Atherosclerosis, Stiff Vessel Disease, Peripheral Vascular Disease, Coronary Heart Disease, Stroke, Myocardial Infarct, Cardiomyopathies, Restenosis Arteriosclerosis is a disease marked by thickening, hardening, and loss of elasticity in arterial walls, of which atherosclerosis is a sub-type. Arteriosclerosis in turn falls within the genus of stiff vessel diseases. In addition, aneurysms may form from localized weakening of the vessel wall and are associated with the development of arteriosclerosis. Without limitation to theory, it is believed that damage to the blood vessels of these diseases results from formation of AGEs, either through irreversible protein cross-linking or the stimulation of bioactive agents, or both. Accordingly, the compounds of the invention are used to treat, prevent, reduce or ameliorate stiff vessel disease, including arteriosclerosis, atherosclerosis and aneurysms. Peripheral vascular disease is an indication that overlaps with atherosclerosis but also covers disease which is believed to have a stronger inflammatory component. Compounds of the invention are used to treat, prevent, reduce or ameliorate peripheral vascular disease. Coronary heart disease is a form of atherosclerosis of the coronary arteries. Compounds of the invention are used to treat, prevent, reduce or ameliorate coronary heart disease.

When the heart pumps blood into the vascular system, the ability of the arteries to expand helps to push blood through the body. When arteries become stiff, as they do in the natural process of aging, the ability of the arteries to expand is diminished which also has consequences for the heart. The heart has to work harder to pump the blood into the stiff arteries, and it eventually hypertrophies (enlarges in size) to accomplish this. A hypertrophied heart is an inefficient pump, and is one of the disorders that leads to congestive heart failure. The compound, 3-[2-phenyl-2-oxoethyl]-4,5-dimethyl-thiazolium chloride salt, showed an ability to reverse the stiffness of arteries and reduce left ventricular mass in Phase IIa clinical trials, as measured by the ratio of stroke volume (ml) to pulse pressure (mm Hg) and echocardiography. Such a compound can be provided by administration of an N-formyl thiazine compound, (i.e., 2-hydroxy-5,6-dimethyl-2-phenyl-2,3-dihydro-(1,4)thiazine-4-carbaldehyde) and conversion of the compound under, for example, acidic conditions in the stomach, to the corresponding thiazolium salt. The potential clinical benefit of this is to lessen the effort that the heart must expend to push blood throughout the body. The effect is also believed to contribute to preventing hypertrophy and subsequent inefficiency of the heart, which inefficiency would contribute to congestive heart failure.

Stroke is a cardiovascular disease that occurs when blood vessels supplying blood (oxygen and nutrients) to the brain burst (hemorraghic stroke) or are obstructed by a blood clot or other particle. Nerve cells in the affected area of the brain die within minutes of oxygen deprivation, and loss of nerve cell function is followed by loss of corresponding bodily function. Of the four main types of stroke, two are caused by blood clots or other particles. The former two are the most common forms of stroke, accounting for about 70-80 percent of all strokes.

Blood clots usually form in arteries damaged by atherosclerosis. When plaque tears from the sheer forces of blood flowing over an uneven, rigid cap atop the plaque site, thrombotic processes become involved at the "injury" site. As a result, clots can form. Compounds of the invention are used to prevent, reduce or ameliorate the risk of stroke in patients who have suffered previous strokes or have otherwise been identified as at risk.

Varicose veins may result from weakness in the vessel walls of veins in the legs. Without limitation to theory, it is believed that damage to the vessels walls of leg veins results from formation of AGEs, either through irreversible protein cross-linking or the stimulation of bioactive agents, or both. The compounds of the invention are used to treat, prevent, reduce or ameliorate varicose veins. The compounds can also be used to treat, prevent, reduce or ameliorate peripheral vascular disease and periarticular rigidity.

Treatment with the compounds of the invention during the relatively immediate aftermath of a heart attack can be used to reduce the size of the myocardial infarct resulting from the heart attack. This treatment is preferably administered within six hours of the heart attack, more preferably, within three hours, most preferably within 1-2 hours of the heart attack. A dose of 0.01-4.0 mg/kg administered orally or 0.01-2.0 mg/kg administered intravenously, preferably within the time period outlined above can be used. Preferred routes of administration include i.v. injection or i.v. drip. Thereafter, optional supplemental administrations can be made with the dosages described below.

Atherosclerosis is a disease that involves deposition of blood lipids in plaque in the arteries throughout the body. In coronary arteries, accumulation of plaque progressively leads to reduced coronary flow, with occlusion of the arteries causing focal death of cardiac tissue (myocardial infarction, heart attack). If the amount of tissue that dies is large enough, death ensues. In a Phase IIa trial, the thiazolium compound, 3-[2-phenyl-2-oxoethyl]-4,5-dimethyl-thiazolium salt, increased the amount of circulating triglycerides (lipids). Consistent with the known presence of AGEs in plaque, the result indicates that the agent had a lipid mobilizing effect on arterial plaque. Reducing local deposits of plaque should eventually lessen the risk of myocardial infarction and death due to heart attacks.

Fibrotic diseases further include diseases that have as a manifestation fibrotic hypertrophy of the heart. These diseases include endomyocardial fibrosis (wherein endocardium and subendocardium are fibrosed, such as in some manifestations of restrictive cardiomyopathy), dilated congestive cardiomyopathy (a disorder of myocardial function with heart failure in which ventricular dilation and systolic dysfunction predominate), hypertrophic cardiomyopathy (characterized by marked ventricular hypertrophy with diastolic dysfunction in the absence of an afterload demand), and other cardiohypertrophies. In dilated congestive cardiomyopathy, typically at presentation there is chronic myocardial fibrosis with diffuse loss of myocytes. In hypertrophic cardiomyopathy, usually the interventricular septum is hypertrophied more than the left ventricular posterior wall (asymmetric septal hypertrophy). Treatment using the invention is expected to treat, prevent, reduce or ameliorate such diseases, or hypertrophy, fibrotic hypertrophy or fibrosis in such diseases.

Hypertrophies of the heart can be diagnosed and monitored by methods known in the art, such as by electrocardiogram, echocardiography or magnetic resonance imaging. Such diagnostic methods can be applied in particular for subjects having a risk factor for such hypertrophy, such as congestive heart failure, prior cardiac surgery or diabetes. In one aspect, the invention comprises identifying cardio-hypertrophy using biophysical diagnostic tools, and administering an active agent of the invention to treat, prevent, reduce or ameliorate such diseases, or hypertrophy, fibrotic hypertrophy or fibrosis in such diseases. The invention can further include monitoring cardio-hypertrophy during the course of treatment with active agent.

Erosion or tearing of arterial wall plaque can occur due to the rough and irregular shape of the plaque as it forms from deposition of lipids and invasion of cells such as monocytes and macrophages (foam cells). When erosion occurs platelets and other components of the blood clotting system are activated, resulting in formation of a clot (thrombus). When the thrombus grows to such a state that blood flow is reduced, severe angina attacks that characterize unstable angina can occur. Plaque forms irregular shapes and in doing so creates shear stresses from the flow of blood over this irregular form. It is the irregularity of plaque shape that leads to the dislodging or tearing of the plaque, and to the subsequent invasion of reactive cells. On the surface of plaque is collagen, which is believed to contribute to the rigidity of the irregular shape. Without limitation to theory, it is believed that reducing the crosslinking of such a rigid collagen cap results in smoother blood flow, with a reduced risk of angina-causing tears. Accordingly, the compounds of the invention are used to treat, prevent, reduce or ameliorate unstable angina.

Faithful conduction of the electrical impulse from the sinoatrial to the atrioventricular nodes depends upon close apposition of myocardial cells. Excess production of collagen in the heart, which occurs naturally with aging but more so in diabetes and in conditions of heart disorders such as hypertension, causes an increase in the distance between myocardial cells, leading to atrial fibrillation. Compounds of the invention are used to treat, prevent, reduce or ameliorate atrial fibrillation.

The fibrotic indications further include restenosis, which is the process of increasing artery closure following an operation to open the artery, such as balloon angioplasty. Renovascular hypertension is the result of one or more of the renal arteries becoming partially or completely occluded. Compounds of the invention are used to treat, prevent, reduce or ameliorate restenosis and renovascular hypertension.

Certain Fibrotic Diseases

Among the indications that can be treated by administration of the compounds of the invention are a number of indications linked to or associated with the formation of excess collagen. Among these, a number of the indications can be termed fibrotic diseases.

Such fibrotic diseases include systemic sclerosis, mixed connective tissue disease, fibrodysplasia, fibrocystic disease, sarcoidosis, myositis (e.g., polymyositis, primary idiopathic polymyositis, childhood polymyositis, dermatomyositis, childhood dermatomyositis, primary idiopathic dermatomyositis in adults, inclusion body myositis, polymyositis or dermatomyositis associated with malignant tumors). Dermatomyositis can be associated with fibrosing or hypertrophic aspects, including fibrosing alveolitis and pulmonary fibrosis. Treatment using the invention is expected to treat, prevent, reduce or ameliorate such diseases or hypertrophy, fibrotic hypertrophy or fibrosis in such diseases. Amelioration includes reducing the rate of progression of a disease.

Among these fibrotic diseases are diseases that have as a manifestation fibrotic vascular intimal hypertrophy. These diseases include vasculitis (including coronary artery vasculitis), polyarteritis nodosa or temporal arteritis. Treatment using the invention is expected to treat, prevent, reduce or ameliorate vascular intimal hypertrophy in such diseases.

These fibrotic diseases further include diseases that have as a manifestation fibrotic hypertrophy of skin and/or muscle tissue. These diseases include scleroderma, eosinophilic fasciitis, discoid lesions associated with lupus or discoid lupus or surgical adhesions. Treatment using the invention is expected to treat, prevent, reduce or ameliorate such indications or hypertrophy or fibrosis of skin or muscle tissue.

Such fibrotic diseases further include diseases that have as a manifestation fibrotic hypertrophy of nerve tissue. These diseases include cerebrosclerosis, annular sclerosis. diffuse sclerosis and lobar sclerosis. Treatment using the invention is expected to treat, prevent, reduce or ameliorate such diseases, or hypertrophy, fibrotic hypertrophy or fibrosis of nerve tissue in such diseases.

These fibrotic diseases further include fibrotic lung diseases that have as a manifestation fibrotic hypertrophy or fibrosis of lung tissue. These diseases include pulmonary fibrosis (or interstitial lung disease or interstitial pulmonary fibrosis), idiopathic pulmonary fibrosis, the fibrotic element of pneumoconiosis (which is associated with exposure to environmental hazards such as smoking, asbestos, cotton lint, stone dust, mine dust and other particles), pulmonary sarcoidosis, fibrosing alveolitis, the fibrotic or hypertrophic element of cystic fibrosis, chronic obstructive pulmonary disease, adult respiratory distress syndrome and emphysema. Treatment using the invention is expected to treat, prevent, reduce or ameliorate such diseases, or hypertrophy, fibrotic hypertrophy or fibrosis in such diseases.

Such fibrotic diseases further include diseases that have as a manifestation fibrotic hypertrophy or fibrosis of prostate, liver, the pleura (e.g., pleurisy, pleural fibrosis) or pancreas. These diseases include benign prostatic hypertrophy (BPH) and fibrosis of the liver. Treatment using the invention is expected to treat, prevent, reduce or ameliorate such diseases, or hypertrophy, fibrotic hypertrophy or fibrosis in such diseases.

These fibrotic diseases further include diseases that have as a manifestation fibrotic hypertrophy or fibrosis of the bowel wall, such as inflammatory bowel disease, including Crohn's disease. Treatment using the invention is expected to treat, prevent, reduce or ameliorate such diseases, or hypertrophy, fibrotic hypertrophy or fibrosis in such diseases.

Bladder Elasticity

Indications that can be treated, prevented, reduced or ameliorated with the compounds of the invention include loss of bladder elasticity. Bladder elasticity is tied to the frequency of urination, and the urgency or sudden desire to urinate. Accordingly, the invention can be used to treat, prevent, reduce or ameliorate non-obstructive uropathy, a disorder characterized by an overactive bladder that entails increased frequency of urination, a strong and sudden desire to urinate (urgency) which may also be associated with involuntary urinary leakage (urge incontinence).

Macular Degeneration

The effect of the compounds of the invention in reducing levels of other endogenous bioactive agents, particularly VEGF and/or TGF[beta], is believed to underlie effectiveness against macular degeneration or macular edema. Again, however, the invention is not limited to theory. Moreover, an anti-fibrotic effect or another effect against tissue hypertrophy may contribute. Treatment using the invention is expected to treat, prevent, reduce or ameliorate macular degeneration or macular edema. In one aspect of the invention, the treatment is used to treat, prevent, reduce or ameliorate the wet form of macular degeneration. In the wet form, new blood vessel growth has a greater contribution to the disease.

Treatment of Glaucoma and Improving Ocular Accomodation

Diabetes is the major determinant to the development of visual disability and blindness in parts of the world unencumbered by causes related to malnutrition or infectious diseases. Retinopathy is the leading cause of blindness in diabetics and is a progressive, degenerative disease. Of the many risk factors believed to be associated with diabetic retinopathy, the level of glucose in the plasma has been widely investigated. It is well accepted that a lower incidence of retinopathy is associated with decreased plasma levels of glucose.

Ophthalmologic disorders in diabetes include opacification and glaucoma. The occurrence of these indications is correlated with the persistent hyperglycemia of the disease. Although the incidence of glaucoma is significant in diabetic populations, glaucoma affects a substantial portion of the general aging population as well.

Primary open angle glaucoma occurs in approximately 4% of diabetics compared to 1.8% of the general population. The reasons for the increase in intraocular pressure that is observed in this disorder are not completely understood. The increase in intraocular pressure that characterizes glaucoma is likely caused by an impairment in the drainage of fluid from the eye at the trabecular meshwork since trabeculectomy restores, at least for a period of time, normal intraocular pressures. The origin of this impairment to fluid movement is currently unknown but may be related to a physical obstruction or restriction to movement of proteins that make up a sieving system in the trabecular meshwork. The trabecular meshwork functions as a sieving system that maintains a restricted flow of intraocular fluid from the eye. The result of excess restriction of this flow is a back pressure that causes increased intraocular pressure.

Glucose reacts with proteins by a non-enzymatic, post-translational modification process called non-enzymatic glycation. The resulting sugar-derived adduct matures to a molecular species that is reactive, and can readily bond to amino groups on adjacent proteins, resulting in the formation of cross-links between proteins related to advanced glycation end products (AGEs) between proteins.

It has now been found that certain compounds that inhibit the formation of such sugar-derived adducts, or in some cases are believed to deactivate such adducts or break resulting crosslinks, can reduce intraocular pressure or ameliorate a trend towards elevated pressure.

Structural matrix proteins isolated from tissues of diabetics and aged individuals are more highly crosslinked than those from nondiabetics or younger individuals and are more resistant to both enzymatic and chemical hydrolysis in vitro. It is this irreversibly cross-linked state of proteins related to AGEs that is believed to cause stiffness of tissues. The cleavage of sugar derived cross-links between proteins can provide a mechanism-based therapy for restoration of normal tissue function. An agent that cleaves sugar derived cross-links between proteins or inhibits their formation can restore more normal sieving function and movement to the trabecular meshwork.

In accordance with the present invention, methods for administering pharmaceutical compositions containing the compounds of the invention have been developed for reducing the intraocular pressure associated with glaucoma.

Pharmaceutical compositions of the invention include administering an intraocular pressure decreasing amount of a compound of the formula I as formulated aqueous droplets or as tablets.

In another embodiment of the invention a method is provided for the treatment of an animal, preferably a mammal, preferably a human with ophthalmologic disorders including glaucoma and reduced accommodation. Briefly the method of the present invention provides for a method of treatment of mammals with glaucoma or reduced accommodation that can be caused by age or certain age-related diseased states such as diabetes. The method provides for administration of classes of inhibitors of advanced glycation. The invention further provides for methods to monitor the improvement in the ocular condition during the course of the administration of compound.

To treat glaucoma or reduced accommodation, and their associated symptoms by administration of an effective amount of a pharmaceutical composition will be recognized by clinicians. The amount includes an amount effective to reduce, ameliorate or eliminate one or more symptoms of the disease sought to be treated or the condition sought to be avoided or treated, or to otherwise produce a clinically recognizable change in the pathology of the disease or condition.

In a preferred embodiment, the pharmaceutically effective amount of the compounds of the invention is approximately 0.1 or 0.5 to 4 mg/kg body weight daily. Still more preferably, the pharmaceutically effective amount is approximately 1 mg/kg body weight daily. In a preferred embodiment, the amount is administered in once daily doses, each dose being approximately 1 mg/kg body weight.

In treating glaucoma, agents of the inventions can be administered concurrently or in a combined formulation with one or more α2-selective adrenergic agonists, carbonic anhydrase inhibitors or prostaglandin analogs. Examples of α2-selective adrenergic agonists include clonidine, apraclonidine, guanfacine, guanabenz and methyldopa, which are administered in effective amounts as is known in the art. Examples of carbonic anhydrase inhibitors include acetazolamide, dichlorphenamide and methazolamide, which are administered in effective amounts as is known in the art. Examples of prostaglandin analogs include PGE2 and PGF2α analogs, which are administered in effective amounts as is known in the art, including effective amounts administered by topical application to the eye. Thus, the invention further provides pharmaceutical compositions comprising an agent of the invention in combination with an effective amount of an α2-selective adrenergic agonist, carbonic anhydrase inhibitor, prostaglandin analog, or combination thereof.

Compounds of the invention can be used in conjunction with monitoring the improvement (decrease) in the intraocular pressure in a mammal using standard methodology.

The methods of the inventions can be assessed in animal models for ophthalmologic function. For example, improvements in fluid outflow facility can be studied in Rhesus monkeys treated with the compounds and methods of the invention. Aged Rhesus monkeys receive a single transcorneal injection of a test compound (compound of the invention) at a concentration of about 1 mM in the anterior chamber of one eye, and Barany's solution, as a control, in the adjacent eye. Needle outflow facility is measured under baseline and pilocarpine-stimulated conditions at time points (for example, 3, 8, 12 and 24 weeks), after the administration of the test compound. Increases in outflow facility in the drug treated vs. the control eye under baseline and cholinergic-stimulated (e.g. pilocarpine) conditions at the various time points are compared. As the enhancement of outflow facility can be influenced by the route of administration of the cholinergic agent, various routes of administration of the cholinergic agent can be used in the experiments. For instance, an intravenous administration versus a direct administration of pilocarpine can be compared. The above experiment demonstrates one method of measuring the improvement in ophthalmologic function. Such improvement has been illustrated with 4,5-dimethyl-3-(2-oxoethyl-phenethyl)thiazolium chloride, a compound that can be obtained in the stomach by administration of administration of a dihydrothiazine compound of the invention. See, copending U.S. patent application Ser. No. 10/038,112, filed Dec. 31, 2001 for "Methods for Treating Glaucoma I," ("the '112 application," which is hereby incorporated by reference).

In addition to measuring increased fluid outflow facility using the methods of the invention, improvements in pilocarpine-stimulated accommodation (i.e., the process of effecting refractive changes in the shape of the lens) can also be assessed in animal studies. As in the regulation of outflow facility, cholinergic input stimulates the movement of the ciliary muscle to control the shape of the lens, and allows accommodation in conditions of low illumination. Accommodation is impaired in a vast majority of individuals and begins to become noticeable to the individual around the age of 40 years. Interestingly, changes in accommodative response occur much earlier in life, around 18 years of age, and progresses until vision is noticeably impaired.

Physiological studies on accommodation are conducted following intraocular injection of a test compound and the results are compared relative to the results of control (untreated) animals. In the experiment, primates (for example, Rhesus monkeys) are treated twice a day for four days with 2 μg of prostaglandin F2α (PGF2α). On days 5-8 both eyes are treated first with 2 μg of PGF2α followed 2 hours later with an intraocular injection of 10 μL of the test compound of a final concentration of 1 mM. No injection is made to the control eye. 24 Hours after the last injection of the test compound, a course of therapy consisting of once a day dosing for a total of 4 days accommodative responses to i.m. pilocarpine administration is performed following phenylephrine refraction. Improvement in accommodation has been illustrated with 4,5-dimethyl-3-(2-oxoethyl-phenethyl)thiazolium chloride. See, for example, the discussion in the '112 application.

Compounds of the invention can be tested to determine corneal penetration to the anterior chamber of the eye following topical administration of eye drops. For example, a test compound is assayed in vitro through an intact rabbit cornea for transcorneal penetration in a standard diffusion chamber apparatus. Corneas are mounted in a chamber at 37° C. with the epithelial side exposed to the test compound in Barany's solution. 1.0 mL samples are taken from the endothelial side 1 hour after addition of the test compound at a final concentration of 1 mM to the epithelial chamber. The volume of the chamber is replaced with phosphate buffered saline. The amount of test compound can be measured using any means that can be used to separate the compound and measure its concentration. For example, an HPLC with an attached UV detector can be used to determine the concentration of the test compound that has penetrated the cornea. Penetration values are also determined at later time points, for example, at 5 hours.

Assessment of corneal penetration of compounds of the invention can be determined in vivo, for example, in Cynomolgus monkeys. During these studies, the penetration of a test compound is evaluated using an eye-cup which holds a solution of 10 mM of the test compound in Barany's solution for 5 hours. At the end of the experiment the eye cup is removed, the eye is repeatedly flooded with Barany's solution and a sample of intraocular fluid is removed from the anterior chamber with a needle inserted through the cornea. The quantity of the test compound in the intraocular fluid is determined using, for example, HPLC methods.

The activity of the compounds of the invention in breaking, reversing or inhibiting the formation of AGE's or AGE-mediated crosslinks can be assayed by any of the methods described in U.S. Pat. No. 5,853,703.

Amyotrophic Lateral Sclerosis (ALS)

ALS is associated with degradations of the motor neuron system and/or the posterior column of the spinal cord. In ALS patients, these structures tend to stain with AGE-reactive antibodies. Treatment using the invention is expected to treat, prevent, reduce or ameliorate ALS.

Rheumatoid Arthritis, Osteoarthritis, Bone Resorption

It is believed, without limitation to such theory, that reducing AGE accumulation at the joints affected by rheumatoid arthritis or osteoarthritis reduces stimulation of the production of cytokines involved in inflammatory processes of the disease. Treatment using the invention is expected to treat, prevent, reduce or ameliorate rheumatoid arthritis or osteoarthritis. Similarly, it is believed that reducing AGE accumulation at bone reduces stimulation of bone resorption. Accordingly, the invention is used to treat, prevent, reduce or ameliorate osteoporosis, bone loss or brittle bone.

Dialysis

The compounds can be administered as part of a dialysis exchange fluid, thereby preventing, limiting or ameliorating the damage to tissue caused by the sugars found in such exchange fluid. For example, the compounds of the invention are expected to prevent, limit or ameliorate the stiffening and sclerosing of peritoneal tissue that occurs in peritoneal dialysis, as well as prevent, limit or ameliorate the formation of new blood vessels in the peritoneal membrane. In hemodialysis, the compounds are expected to prevent, limit or ameliorate the stiffening and sclerosing of red blood cells and vasculature resulting from exposure to the sugars exchanged into the blood during dialysis. Exchange fluids for peritoneal dialysis typically contain 10-45 g/L of reducing sugar, typically 25 g/L, which causes the formation of AGEs and consequent stiffening and degradation of peritoneal tissue. Similarly, hemodialysis fluids typically contain up to about 2.7 g/L of reducing sugar, typically 1 to 1.8 g/L. Thus, the invention provides methods by which the compounds of the invention are provided in these fluids and thereby prevent, limit or ameliorate the damage that would otherwise result. Alternatively, the invention provides methods whereby the compounds of the invention are administered by the methods described below to prevent, limit or ameliorate such damage from dialysis. In hemodialysis, the exchange fluid preferably contains 0.006-2.3 mg/L of an agent of the invention, more preferably, 0.06 to 1.0 mg/L. In peritoneal dialysis, the exchange fluid preferably contains 0.01 to 24 mg/L of an agent of the invention, or preferably, 1.0 to 10 mg/L.

Asthma

It is believed, without limitation to such theory, that the compounds of the invention act to prevent, reduce or ameliorate the small but significant thickening of the lung airways associated with asthma. Moreover, the compounds are believed to reduce stimulation of the production of cytokines involved in inflammatory processes of the disease. Accordingly, the compounds are used to treat, prevent, reduce or ameliorate asthma. In this embodiment, one preferred route of administration is pulmonary, such as via an aerosol, though peroral administration is also preferred.

Carpal Tunnel Syndrome

It is believed, without limitation to such theory, that the compounds of the invention act to prevent, reduce or ameliorate fibrotic and cytokine-induced elements of carpal tunnel syndrome. Accordingly, the compounds are used to treat, prevent, reduce or ameliorate carpal tunnel syndrome.

Fibrotic diseases also include Dupuytren's contracture, a contracture of the palmar fascia often causing the ring and little fingers to bend into the palm. Administration of the compounds of the invention is expected to treat, prevent, reduce or ameliorate Dupuytren's contracture, or hypertrophy, fibrotic hypertrophy or fibrosis in Dupuytren's contracture.

In these embodiments, one preferred route of administration is local injection.

Periodontal Disease

The incidence of periodontal disease is higher in subjects with either insulin-deficient or insulin-resistant diabetes, with consequent hyperglycemia. Again, without limitation to such theory, it is believed that the compounds of the invention can be administered to act, prevent, reduce or ameliorate AGE-induced cytokine action to create or exacerbate periodontal disease. Accordingly, the compounds of the invention are used to treat, prevent, reduce or ameliorate periodontal disease. In this embodiment, one preferred primary or supplemental route of administration is via mouthwash, or compositions adapted for delivery into the subgingival periodontal pocket (such as implants and erodible microspheres). Peroral administration is again useful. The mouthwash preferably contains 0.003-1.0 mg/L of a compound of the invention, more preferably, 0.01-0.1 mg/L.

Sickle Cell Anemia

It is believed, without limitation to such theory, that the compounds of the invention act to prevent, reduce or ameliorate the restraint on blood flow caused by sickling. Again without limitation to theory, the mode of action is believed to be in reducing vascular as well as blood cell inelasticity. Accordingly, the compounds of the invention are used to treat, prevent, reduce or ameliorate sickle cell anemia.

Erectile Dysfunction

Fibrotic diseases further include diseases that have as a manifestation fibrotic disease of the penis, including Peyronie's disease (fibrosis of the cavernous sheaths leading to contracture of the investing fascia of the corpora, resulting in a deviated and painful erection). Administration of the compounds of the invention is expected to treat, prevent, reduce or ameliorate such diseases, or hypertrophy, fibrotic hypertrophy or fibrosis in such diseases.

Without limitation to theory, it is believed that the compounds act to prevent, reduce or ameliorate inelasticity of tissue of the penis and/or fibrosis of tissue of the penis, such as inelasticity or fibrosis of the cavernous sheaths leading to contracture of the investing fascia of the corpora. At least partial restoration of the resulting inelasticity is believed to facilitate engorgement of the corpora cavernosa with blood. Accordingly, the compounds of the invention are used to treat, prevent, reduce or ameliorate erectile dysfunction.

Limited Joint Mobility

Limited Joint Mobility (LJM) is a disorder associated with diabetes and typically involves the joints of the hands. The fourth and fifth fingers are affected initially by limitation of motion. AGE glycation and crosslinking of tendons (collagen) in the joints is believed to contribute to the disease. It is believed, without limitation to theory, that the compounds of the invention act to prevent, reduce or ameliorate inelasticity, fibrous tissue or cytokine-induced inflammation associated with limited joint mobility. Accordingly, the compounds are used to treat, prevent, reduce or ameliorate limited joint mobility.

Antineoplastic Applications

The compounds of the invention inhibit the stimulated formation of bioactive agents, such as VEGF, associated with angiogenesis. Angiogenesis is critical for both normal development and the growth and metastasis of solid tumors. Accordingly, the compounds are used to treat, prevent, reduce or ameliorate the growth of neoplasms by limiting the formation of blood vessels needed to sustain the neoplasms.

End Stage Renal Disease, Diabetic Nephropathy

Diabetic Nephropathy is a complication of diabetes that evolves early, typically before clinical diagnosis of diabetes is made. The earliest clinical evidence of nephropathy is the appearance of low but abnormal levels (>30 mg/day or 20 µg/min) of albumin in the urine (microalbuminuria), followed by albuminuria (>300 mg/24 h or 200 µg/min) that develops over a period of 10-15 years. In patients with type 1 diabetes, diabetic hypertension typically becomes manifest early on, by the time that patients develop microalbuminuria. Once overt nephropathy occurs, the glomerular filtration rate (GFR) falls over several years resulting in End Stage Renal Disease (ESRD) in 50% of type 1 diabetic individuals within 10 years and in >75% of type 1 diabetics by 20 years of onset of overt nephropathy. Albuminuria (i.e., proteinuria) is a marker of greatly increased cardiovascular morbidity and mortality for patients with either type 1 or type 2 diabetes.

Without limitation to theory, it is believed that damage to the glomeruli and blood vessels of the kidney is due to AGE-caused damage, either through protein cross-linking or the stimulation of bioactive agents, or both. Accordingly, the compounds of the invention are used to treat, prevent, reduce or ameliorate damage to kidney in patients at risk for ESRD. The compounds can also be used to treat, prevent, reduce or ameliorate glomerulosclerosis.

Retinopathy

The effect of diabetes on the eye is called diabetic retinopathy and involves changes to the circulatory system of the retina. The earliest phase of the disease is known as background diabetic retinopathy wherein the arteries in the retina become weakened and leak, forming small, dot-like hemorrhages. These leaking vessels often lead to swelling or edema in the retina and decreased vision. The next stage is proliferative diabetic retinopathy, in which circulation problems cause areas of the retina to become oxygen-deprived or ischemic. New vessels develop as the circulatory system attempts to maintain adequate oxygen levels within the retina. Unfortunately, these new vessels hemorrhage easily. In the later phases of the disease, continued abnormal vessel growth and scar tissue may cause serious problems such as retinal detachment. The compounds of the invention are used to treat, prevent, reduce or ameliorate diabetic retinopathy. The compounds can be administered by the methods described below, including by topical administration to the eye. The compounds can also be administered by intravitreal implant.

Cataracts, Other Damage to Lens Proteins

AGE-mediated crosslinking and/or fibrotic processes are believed to contribute to cataract formation and formation of other damage to lens proteins. Compounds of the invention are used to treat, prevent, reduce or ameliorate cataracts or other damage to lens proteins.

Alzheimer's Disease

Considerable evidence exists implicating AGEs that form in the neurofibrillary tangles (tau protein) and senile plaques (beta-amyloid peptide) in early neurotoxic processes of Alzheimer's disease and other neurodegenerative diseases such as Parkinson's disease. Insoluble human tau protein is likely crosslinked. Glycation of insoluble tau from AD patients and experimentally AGE-modified tau generate oxygen free radicals, resulting in the activation of transcription via nuclear factor-kappa B, and resulting in an increase in amyloid beta-protein precursor and release of amyloid beta-peptides. Thus, AGE-modified tau may function as an initiator in a positive feedback loop involving oxidative stress and cytokine gene expression. Compounds of the invention are used to treat, prevent, reduce or ameliorate Alzheimer's disease and other neurodegenerative diseases such as Parkinson's disease.

Other Indications

For reasons analogous to those set forth above, the invention is believed to be useful in treating, preventing, reducing or ameliorating diabetes or its associated adverse sequelae, and peripheral neuropathy. The agents, especially in topical form, increase elasticity and/or reduce wrinkles in skin. The agents further increase red blood cell deformability.

Combination Therapies

In cardiovascular therapies, the compounds of the invention can be administered concurrently or in a combined formulation with one or more antioxidants. Examples of appropriate antioxidants are vitamin A, vitamin B6, vitamin C, vitamin E, glutathione, β-carotene, α-lipoic acid, coenzyme Q10, selenium and zinc, which are administered in effective amounts as is known in the art. Thus, the invention further provides pharmaceutical compositions comprising an agent of the invention in combination with an effective amount of an antioxidant.

In treating hypertension, heart failure, cardiomyopathy or heart attack, the compounds of the invention can be administered concurrently or in a combined formulation with one or more angiotensin converting enzyme (ACE) inhibitors, angiotensin II receptor antagonists, calcium channel blockers, diuretics, digitalis or beta blockers. Examples of ACE inhibitors include Captopril, Enalapril, Enalaprilat, Quinapril, Lisinopril and Ramipril, which are administered in effective amounts as is known in the art. Examples of angiotensin II receptor antagonists include Losartan, Irbesartan, Eprosartan, Valsartan and Candesartan, which are administered in effective amounts as is known in the art. Examples of calcium channel blockers include Amlopdipine, Bepridil, Diltiazem, Felodipine, Isradipine, Nicardipine, Nifedipine, Nimodipine and Verapamil, which are administered in effective amounts as is known in the art. Among diuretics, preferred examples include Furosemide, Bumetanide, Torsemide, Ethacrynic acid, Azosemide, Muzolimine, Piretanide, Tripamide and Hydrochlorothiazide, which are administered in effective amounts as is known in the art. Examples of beta adrenergic antagonists include Metoprolol, Carvedilol, Bucindolol, Atenolol, Esmolol, Acebutolol, Propranolol, Nadolol, Timolol, Pindolol, Labetalol, Bopindolol, Carteolol, Penbutolol, Medroxalol, Levobunolol, Bisoprolol, Nebivolol, Celiprolol and Sotalol, which are administered in effective amounts as is known in the art. Thus, the invention further provides pharmaceutical compositions comprising an agent of the invention in combination with an effective amount of an ACE inhibitor, diuretic, digitalis, beta blocker, or combination thereof.

For treating diabetes or complications thereof, the invention further provides pharmaceutical compositions comprising an agent of the invention in combination with an effective amount of a thiazolidinedione or "glitazone" diabetes drug, such as Troglitazone, Rosiglitazone, and Pioglitazone.

In treating atherosclerosis, compounds of the invention can be administered concurrently or in a combined formulation with one or more statins (HMG CoA reductase inhibitors) or cholestyramine. Examples of statins include Mevastatin, Lovastatin, Simvastatin, Pravastatin and Fluvastatin, which are administered in effective amounts as is known in the art. Thus, the invention further provides pharmaceutical compositions comprising an agent of the invention in combination with an effective amount of a statin, cholestyramine, or both.

For a number of indications discussed, including sickle cell anemia and diabetic complications, as well as wound healing and any other indication in which increased tissue perfusion is a useful means or adjunct to therapy, the compounds of the invention can be administered with erythropoietin, which is administered in effective amount as is known in the art. Erythropoietin includes stable forms of erythropoietin such as are marketed by Amgen (Thousand Oaks, Calif.).

The following examples further illustrate the present invention, but of course, should not be construed as in any way limiting its scope.

EXAMPLES

Example 1

Preparation of 2-Hydroxy-5,6-Dimethyl-2-Phenyl-2, 3-Dihydro-(1,4)thiazine-4-carbaldehyde (Ia)

In a 1-L three-necked flask equipped with a mechanical stirrer was charged 4,5-dimethyl-3-(2-oxo-2-phenylethyl)-thiazolium chloride (26.75 g, 0.1 mole) in water (500 mL) at room temperature. 2N Sodium hydroxide solution (approximately 60 mL) was slowly fed into the reaction flask. No temperature change was observed to accompany the addition. At this point, white solids had precipitated from solution (the pH of the solution was about 12). After about 10 minutes stirring, the mixture was filtered through a sintered glass funnel. The filter cake was washed twice with water and was dried overnight on the funnel. After dying overnight in the oven 18.86 g of the title compound (Ia) was recovered, representing a 75.6% yield of thiazine.

A portion (2.3 g) of the recovered product was recrystallized from acetonitrile (50 mL) to yield 1.68 g of a yellowish-white product. Further purification of a portion (0.9 g) of the yellowish-white product was accomplished by recrystallization with acetonitrile (20 mL) using decolorizing carbon to provide 0.67 g of a white solid: mp=118-122° C.

HPLC 99% on YMC, C-18, ODS-A column, 50 mm×4.6 mm ID, S-5 µm, solvent A water solvent B was acetonitrile.

$^1$H NMR (400 MHz, CDCl$_3$) δ 8.69-8.00 (d, 1H, CHO), 7.65-7.6 (m, 2H, aromatic), 7.4-7.32 (m, 3H, aromatic), 4.82-3.07 (4 d, 2H, CH$_2$, J=12.82 and 13.18), 3.81-3.73 (broad, ~1H, OH), 2.21-1.92 (2 double peaks, 6H, CH$_3$)

$^{13}$C NMR (100 MHz CDCl$_3$) 163.7 and 161.43 (2×CO), 140.97, 140.57, 128.64, 128.57, 126.16, 126.01, 125.39, 122.66, 116.86, 112.20, 82.87, 82.35, 56.49 and 49.68 (CH$_2$), 18.72 and 17.90 (CH$_3$), 17.23 and 17.12 (CH$_3$)

Due to the existence of two rotamers two sets of signals were observed in the proton and carbon spectra.

MS (FAB) m/Z 250 (M$^+$), 232 (M-H$_2$O)

Anal. Calcd. for C$_{13}$H$_{15}$NO$_2$S: C, 62.63; H, 6.06; N 5.62; S 12.86. Found: C, 62.48; H, 6.06; N 5.79; S 12.84.

Example 2

Conversion of 2-Hydroxy-5,6-Dimethyl-2-Phenyl-2,3-Dihydro-(1,4)thiazine-4-carbaldehyde to 4,5-Dimethyl-3-(2-oxo-2-phenyl-ethyl)-thiazolium chloride under Acidic Conditions The following experiment provides evidence that thiazine structures related to compound Ia can be converted under acidic conditions to thiazolium structures, and thus can serve as pro-drug forms of thiazolium agents.

Compound Ia (2.48 mmol, 0.620 g) was weighed into a 100 mL round bottom flask equipped with magnetic stir bar. Methanol (40 mL) was added, and the solution was stirred until all solid was dissolved. Aqueous hydrochloric acid was added (1N, 3.968 mmol, 4.0 mL) and the reaction solution stirred at ambient temperature for 48 hours. The methanol was removed in vacuo, and the residue was diluted with 25 mL of distilled water. The aqueous layer was extracted with methyl t-butyl ether (2×20 mL). The aqueous layer was concentrated to dryness in vacuo and the residue was crystallized with acetonitrile, methyl-t-butyl-ether, (1:1). The crystals were collected via filtration to give 598 mg (90% yield) of 4,5-dimethyl-3-(2-oxo-2-phenylethyl)-thiazolium chloride. The crystals were re-crystallized (acetonitrile/methyl-t-butyl ether, 1:1) to give 411 mg of a white solid (mp 212° C. (dec)).

$^1$H NMR: (400 MHz, DMSO-$d_6$) δ 10.112 (s, 1H), 8.072 (d, 2H), 7.794 (t, 1H), 7.659 (t, 2H), 6.513 (s, 2H), 2.547 (s, 3H), 2.320 (s, 3H).

Elemental Analysis calculated for $C_{13}H_{14}ClNOS$: C, 58.31; H, 5.27; Cl, 13.24; N, 5.23; S, 11.97. Found: C, 57.99; H, 5.07; Cl, 13.34; N, 5.15; S, 11.88.

MS (FAB): Calculated for $C_{13}H_{14}ClNOS$, MW=267.78. Found: m/z 232 (M-Chlorine, parent ion).

Example 3

Conversion of 2-Hydroxy-2-Phenyl-2,3-Dihydro-(1,4)thiazine-4-carbaldehyde (Ib) to 3-(2-oxo-2-phenyl-ethyl)-thiazolium chloride under Acidic Conditions In a 15 mL round bottom flask, stirred with a magnetic stirrer, was charged 36 mg (0.16 mmol) of compound Ib (prepared as described by Thornalley et al., Biochemical Pharmacology, vol. 57, pp 303-308, 1999), 2 mL of 1% hydrochloric acid and 2 mL of Ethyl Acetate. Since there was no reaction as monitored by HPLC, 2 mL of 5N Hydrochloric acid, and 2 mL of methanol was added, and the flask was heated to 35° C. After about 15 h the reaction was finished based on the HPLC. The reaction product was concentrated, water was added, and extracted with methyl t-butyl ether, and the aqueous was again concentrated to dryness. The $^1$H NMR (400 MHz, DMSO) showed the characteristic singlet proton (1 H) for the 2 H thiazole at 10.3 ppm and singlet methylene (2H) alpha to the carbonyl and alpha to immonium group at 6.5 ppm.

Where noted above, publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A compound of the formula:

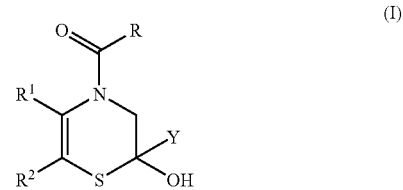

wherein:

R is hydrogen, methyl, hydroxymethyl or α-hydroxyethyl;

$R^1$ and $R^2$ are independently selected from hydrogen, $C_1$-$C_6$ alkyl, $C_1$-$C_6$ hydroxyalkyl, $C_3$-$C_8$ cycloalkyl, $C_1$-$C_6$ alkenyl, $C_1$-$C_6$ alkynyl, amino, monoalkylamino, dialkylaminoalkyl, and pyrrolidin-1-ylalkyl; and Y is selected from the group consisting of $C_1$-$C_6$ alkyl, and substituted and unsubstituted aryl, wherein substituted aryl is substituted with one to three substituents selected from amino, $C_1$-$C_6$ alkylamino, $C_1$-$C_6$ dialkylamino, $C_1$-$C_6$ alkoxy, $C_1$-$C_6$ alkyl, cyano, nitro, $C_1$-$C_6$ mono, di- or trifluoroalkyl, nitro, fluoro, chioro and bromo;

with the provisos that:

(a) if Y is aryl, then at least one of $R^1$ and $R^2$ is other than hydrogen, and (b) if $R^2$ is other than methyl;

or a pharmaceutically acceptable salt thereof.

2. The compound of claim 1, wherein $R^1$ and $R^2$ are independently selected from $C_1$-$C_6$ alkyl, $C_1$-$C_6$ hydroxyalkyl, $C_3$-$C_8$ cycloalkyl, $C_1$-$C_6$ alkenyl, $C_1$$C_6$ alkynyl, amino, monoalkylamino, dialkylaminoalkyl, and pyrrolidin-1-ylalkyl.

3. The compound of claim 2, wherein R is hydrogen, hydroxymethyl or α-hydroxyethyl.

4. The compound of claim 1, wherein at least one of $R^1$ and $R^2$ is $C_1$-$C_6$ alkyl.

5. The compound of claim 4, wherein at least one of $R^1$ and $R^2$ is methyl.

6. The compound of claim 4, wherein Y is selected from the group consisting of substituted and unsubstituted phenyl.

7. The compound of claim 6, wherein Y is unsubstituted phenyl.

8. The compound of claim 7; 2-hydroxy-5,6-dimethyl-2-phenyl-2,3-dihydro-(1, 4)-thiazine-4-carbaldehyde.

9. The compound of claim 7, wherein R is α-hydroxyethyl and $R^1$ and $R^2$ are both methyl.

10. The compound of claim 1, wherein at least one of $R^1$ and $R^2$ is $C_1$-$C_6$ hydroxyalkyl.

11. The compound of claim 10, wherein at least one of $R^1$ and $R^2$ is 2-hydroxyethyl.

12. The compound of claim 1, wherein Y is substituted aryl.

13. A pharmaceutical composition comprising a pharmaceutically effective amount of a compound of the formula:

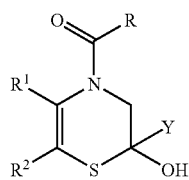

(I)

wherein:
R is hydrogen, methyl, hydroxymethyl or α-hydroxyethyl;
$R^1$ and $R^2$ are independently selected from hydrogen, $C_1$-$C_6$ alkyl, $C_1$-$C_6$ hydroxyalkyl, $C_3$-$C_8$ cycloalkyl, $C_1$-$C_6$ alkenyl, $C_1$-$C_6$ alkynyl, amino, monoalkylamino, dialkylaminoalkyl, and pyrrolidin-1-ylalkyl; and
Y is selected from the group consisting of $C_1$-$C_6$ alkylamino, $C_1$-$C_6$ dialkylamino, $C_1$-$C_6$ alkoxy, $C_1$-$C_6$ alkyl, cyano, nitro, $C_1$-$C_6$ mono, di- or trifluoroalkyl, nitro, fluoro, chloro and bromo;
or a pharmaceutically acceptable salt thereof; and
a pharmaceutically acceptable carrier.

14. The pharmaceutical composition of claim 13, wherein at least one of $R^1$ and $R^2$ is other than hydrogen, and if $R^2$ is hydrogen $R^1$ is other than methyl.

15. The pharmaceutical composition of claim 14, wherein R is hydrogen, $R^1$ and $R^2$ are both methyl and Y is unsubstituted phenyl.

16. The pharmaceutical composition of claim 14, wherein R is α-hydroxyethyl, $R^1$ and $R^2$ are both methyl and Y is unsubstituted phenyl.

17. A method for preparing a compound of the formula:

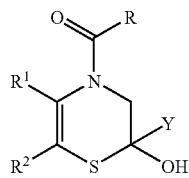

(I)

comprising:
treating a thiazolium compound of the formula:

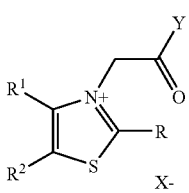

(II)

wherein:
R is hydrogen, methyl, hydroxymethyl or α-hydroxyethyl;
$R^1$ and $R^2$ are independently selected from hydrogen, $C_1$-$C_6$ alkyl, $C_1$-$C_6$ hydroxyalkyl, $C_3$-$C_8$ cycloalkyl, $C_1$-$C_6$ alkenyl, $C_1$-$C_6$ alkynyl, amino, monoalkylamino, dialkylaminoalkyl, and pyrrolidin-1-ylalkyl; and
Y is selected from the group consisting of a substituted and unsubstituted aryl, wherein substituted aryl is substituted with one to three substituents selected from amino, $C_1$-$C_6$ alkylamino, $C_1$-$C_6$ dialkylamino, $C_1$-$C_6$ alkyl, cyano, nitro, $C_1$-$C_6$ mono, di- or trifluoroalkyl, nitro, fluoro, chioro and bromo; and X- is an anion;
with the provisos that:
(a) if Y is aryl, then at least one of $R^1$ and $R^2$ is other than hydrogen, and
(b) if $R^2$ is hydrogen $R^1$ is other than methyl; with an aqueous alkaline solution to afford the compound of the formula I.

18. The method of claim 17, wherein the pH of the aqueous alkaline solution is at least 8.

19. The method of claim 18, wherein the pH of the aqueous alkaline solution is between 9 and 11.

20. The method of claim 17, wherein R is hydrogen, $R^1$ and $R^2$ are both methyl and Y is unsubstituted phenyl.

21. A method of treating a mammal having an indication, wherein the indication is selected from hypertension, reduced vascular compliance, diastolic dysfunction, heart failure, comprising: administering an effective amount of the compound of claim 1 to the mammal.

22. The method of claim 21, wherein the indication is hypertension.

23. The method of claim 22, wherein the hypertension is isolated systolic hypertension.

24. The method of claim 22, wherein the hypertension is systolic hypertension.

25. The method of claim 21, wherein the indication is reduced vascular compliance.

26. The method of claim 21, wherein the indication is diastolic dysfunction.

27. The method of claim 21, wherein the indication is heart failure.

28. The method of claim 21, wherein the indication is diastolic heart failure.

* * * * *